United States Patent [19]

Kisida et al.

[11] Patent Number: 4,596,890
[45] Date of Patent: Jun. 24, 1986

[54] BENZOYLUREAS, AND THEIR PRODUCTION AND USE

[75] Inventors: Hirosi Kisida; Sumio Nishida, both of Takarazuka; Toshihiko Yano, Ikoma, all of Japan

[73] Assignee: Sumitomo Chemical Company, Limited, Osaka, Japan

[21] Appl. No.: 654,161

[22] Filed: Sep. 25, 1984

[30] Foreign Application Priority Data

Oct. 31, 1983 [JP] Japan ................. 58-205361

[51] Int. Cl.⁴ .......................................... C07C 127/22
[52] U.S. Cl. ....................................................... 564/44
[58] Field of Search ................................... 564/44, 23

[56] References Cited

U.S. PATENT DOCUMENTS 3,748,356  7/1973  Wellinga et al. .
4,005,223  1/1977  Sirrenberg et al. .
4,310,548  1/1982  Ehrenfreund ......................... 564/44

FOREIGN PATENT DOCUMENTS 44410  1/1982  European Pat. Off. .
74074  3/1983  European Pat. Off. .
57888  8/1982  European Pat. Off. ............ 564/44
50-38357  3/1980  Japan .
2258  1/1982  Japan ................................... 564/44

Primary Examiner—Charles F. Warren
Assistant Examiner—R. A. Picard
Attorney, Agent, or Firm—Birch, Stewart, Kolasch & Birch

[57] ABSTRACT

A benzoylurea compound of the formula:

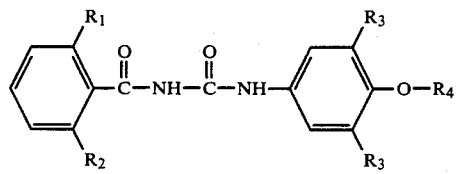

wherein $R_1$ is a hydrogen atom or a halogen atom, $R_2$ is a halogen atom, $R_3$ is a halogen atom or a lower alkyl group and $R_4$ is a 3,5-difluorophenyl group, a pentafluorophenyl group or a pentachlorophenyl group, which is useful as an insecticidal agent.

15 Claims, No Drawings

BENZOYLUREAS, AND THEIR PRODUCTION AND USE

The present invention relates to benzoylureas, and their production and use. More particularly, it relates to benzoylureas of the formula:

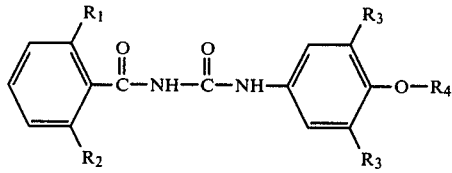

wherein $R_1$ is a hydrogen atom or a halogen atom, $R_2$ is a halogen atom, $R_3$ is a halogen atom or a lower alkyl group and $R_4$ is a 3,5-difluorophenyl group, a pentafluorophenyl group or a pentachlorophenyl group, and their production and use as insecticides.

In the above definitions, the term "halogen" includes chlorine, bromine, fluorine, iodine, etc. The term "lower alkyl" is intended to mean alkyl having not more than 8 carbon atoms, preferably not more than 5 carbon atoms, more preferably not more than 3 carbon atoms.

Among the benzoylureas (I), preferred are those wherein $R_1$ is a hydrogen atom or a fluorine atom, $R_2$ is a fluorine atom or a chlorine atom, $R_3$ is a chlorine atom or a methyl group and $R_4$ is a 3,5-difluorophenyl group or a pentafluorophenyl group.

As a result of extensive study for development of excellent insecticides, it has been found that the benzoylureas (I) exhibit a higher insecticidal activity against larvae of harmful insects such as Lepidoptera (e.g. diamondback moth, rice stem borer, cutworms, armyworms), Diptera (e.g. common mosquito, house fly) and Coleoptera. Advantageously, the benzoylureas (I) can be produced at a relatively low cost. The present invention is based on the above finding.

Some kinds of benzoylurea derivatives including diflubenzuron (U.S. Pat. No. 3,748,356) and 3-(2,6-difluorobenzoyl)-1-[4-(3,5-dichlorophenoxy)phenyl]urea (EP-57888A) are known to be useful as insecticides. The insecticidal potency of the benzoylureas (I) is much higher than that of those known benzoylurea derivatives.

The benzoylureas (I) of the present invention can be produced, for instance, by the procedures as set forth below.

Procedure (A)

The benzoylurea (I) is obtained by reacting a benzoyl isocyanate compound of the formula:

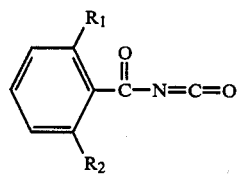

wherein $R_1$ and $R_2$ are each as defined above with an aniline compound of the formula:

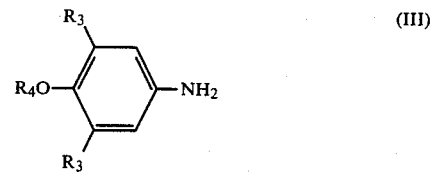

wherein $R_3$ and $R_4$ are each as defined above.

Procedure (B)

The benzoylurea (I) is obtained by reacting a benzamide compound of the formula:

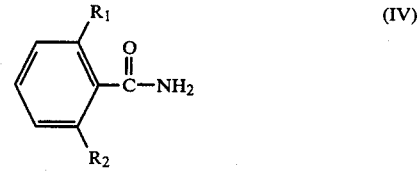

wherein $R_1$ and $R_2$ are each as defined above with an isocyanate compound of the formula:

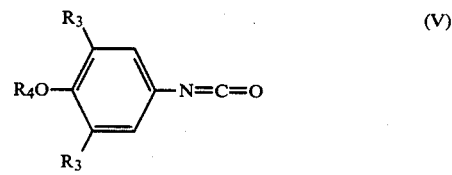

wherein $R_3$ and $R_4$ are each as defined above.

In Procedure (A) or (B), the reaction can be advantageously carried out in the presence of an inert solvent. Specific examples of the inert solvent are hydrocarbons (e.g. benzene, toluene, xylene), halogenated hydrocarbons (e.g. chlorobenzene, carbon tetrachloride, chloroform, methylene chloride, 1,2-dichloroethane), nitrated hydrocarbons (e.g. nitromethane), ethers (e.g. diethyl ether, tetrahydrofuran, dioxane), ketones (e.g. acetone, methyl ethyl ketone, methyl isobutyl ketone), organic polar solvents (e.g. dimethylsulfoxide, dimethylformamide, sulforan), etc. These solvents may be used alone or in combination.

The reaction is normally accomplished under an autogenic or atmospheric pressure within a period of 1 to 50 hours. The two starting compounds or reagents in each reaction, i.e. the compounds (II) and (III) or the compounds (IV) and (V), are usually employed in an equimolar proportion, but either one of them may be used in an excess amount.

The reaction temperature in Procedure (A) is not particularly limitative, although it may be generally from 0° to 80° C., preferably from room temperature to 60° C. Likewise, the temperature in Procedure (B) is not limitative and may be generally from room temperature to 160° C., preferably from 80° to 130° C.

Recovery of the benzoylurea (I) from the reaction mixture may be effected in a per se conventional manner. When desired, the recovered bnezoylurea (I) may be purified by a per se conventional procedure such as chromatography or recrystallization.

The benzoyl isocyanate compound (II) and the benzamide compound (IV) used as the starting compounds in the foregoing reactions are known. The aniline compound (III) and the isocyanate compound (V) are novel, and the aniline compound (III) may be produced, for instance, as set forth below:

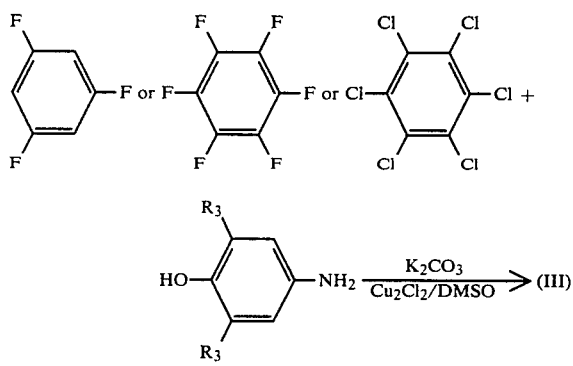

while the isocyanate compound (V) is easily obtainable from the aniline compound (III) by reacting with phosgene.

Practical and presently preferred embodiments of the process for production of the benzoylurea (I) are illustratively shown in the following Examples:

REFERENCE EXAMPLE 1

A mixture of 4-amino-2,6-dimethylphenol (6.92 g), 1,3,5-trifluorobenzene (10.00 g), anhydrous potassium carbonate (13.93 g) and anhydrous cuprous chloride (0.50 g) in dry dimethylsulfoxide (100 ml) was heated under reflux for 4 hours, whereby the inner temperature raised from 120° C. to 150° C. After completion of the reaction, the reaction mixture was cooled to room temperature, and cold water (200 ml) and toluene (100 ml) were added thereto. After continuation of stirring for 30 minutes, the resultant mixture was filtered on celite to remove insoluble materials. The toluene layer was washed with water, dried over anhydrous sodium sulfate and concentrated under reduced pressure. The residue was purified by silica gel chromatography using a mixture of methylene chloride and n-hexane (1:1) as an eluting solvent to give 9.50 g of 4-(3,5-difluorophenoxy)3,5-dimethylaniline as yellowish white crystals. M.P., 67.6° C.

In the same manner as in Reference Example 1, the following aniline compounds were produced:

| Structure | M.P. (°C.) |
|---|---|
| F,F / Cl,Cl aryl ether NH2 | 79.5 |
| F,F,F / Cl,Cl aryl ether NH2 | 91.1 |
| F,F,F / H3C,H3C aryl ether NH2 | 77.3 |
| Cl,Cl,Cl,Cl / Cl,Cl,Cl aryl ether NH2 | 168.2 |

EXAMPLE 1

To a solution of 4-(3,5-difluorophenoxy)-3,5-dimethylaniline (0.200 g) in toluene (20 ml), there was dropwise added a solution fo 2,6-difluorobenzoyl isocyanate (0.147 g) in toluene (10 ml) while stirring for 10 minutes. The resultant mixture was stirred at room temperature overnight. n-Hexane (50 ml) was added thereto. Insoluble materials were collected by filtration and washed with n-hexane to give 0.329 g of N-2,6-difluorobenzoyl-N'-4-(3,5-difluorophenoxy)-3,5-dimethylphenylurea as white powders. M.P., 181.0° C.

EXAMPLE 2

A mixture of 2,6-difluorobenzamide (0.157 g) and 4-(3,5-difluorophenoxy)-3,5-dichlorophenyl isocyanate (0.316 g) in xylene (30 ml) was heated under reflux for 24 hours. After completion of the reaction, the reaction mixture was cooled, and the precipitated crystals were collected by filtration. The collected crystals were recrystallized from acetone to give 0.330 g of N-2,6-difluorobenzoyl-N'-4-(3,5-difluorophenoxy)-3,5-dichlorophenylurea as white crystals. M.P., 201.7° C.

In the same manner as above, there were produced the benzoylureas (I) as shown in Table 1.

TABLE 1

General structure (I): R1,R2-phenyl-C(O)-NH-C(O)-NH-phenyl(R3,R3)-O-R4

| Compound No. | $R_1$ | $R_2$ | $R_3$ | $R_4$ | Physical constant |
|---|---|---|---|---|---|
| 1 | F | F | CH3 | 3,5-difluorophenyl | M.P. 181.0° C. |
| 2 | F | F | Cl | 3,5-difluorophenyl | M.P. 201.7° C. |

TABLE 1-continued

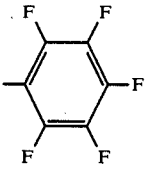

| Compound No. | R₁ | R₂ | R₃ | R₄ | Physical constant |
|---|---|---|---|---|---|
| 3 | F | F | Cl | 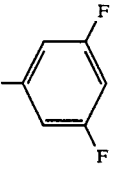 | M.P. 230.6° C. |
| 4 | H | Cl | CH₃ | 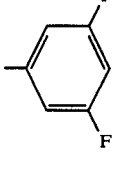 | M.P. 168.7° C. |
| 5 | H | Cl | Cl | 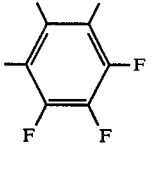 | M.P. 131.2° C. |
| 6 | H | Cl | Cl | 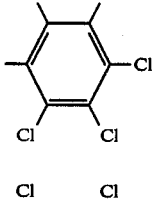 | M.P. 178.4° C. |
| 7 | H | Cl | Cl | 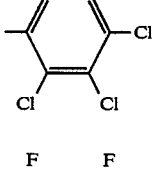 | M.P. 224.0° C. |
| 8 | F | F | Cl | 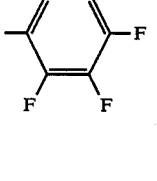 | M.P. 273–275° C. |
| 9 | F | F | CH₃ | 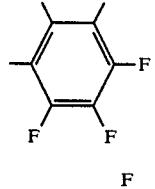 | M.P. 208.6° C. |

TABLE 1-continued

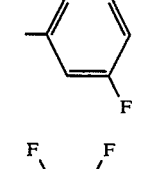

| Compound No. | R₁ | R₂ | R₃ | R₄ | Physical constant |
|---|---|---|---|---|---|
| 10 | H | Cl | CH₃ | 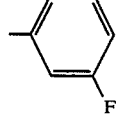 | M.P. 192.5° C. |
| 11 | F | Cl | CH₃ |  | M.P. 191.6° C. |
| 12 | F | Cl | CH₃ | 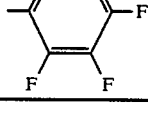 | M.P. 216.6° C. |

On the application of the benzoylureas (I) as insecticides, they may be used as such or in the form of appropriate compositions such as emulsifiable concentrates, wettable powders, dusts, granules, oils, aerozoles, heating fumigants, baits, etc. The content of the benzoylureas (I) in such compositions is usually from about 0.01 to 95% by weight.

The composition can be formulated in a per se conventional manner by mixing at least one of the benzoylureas (I) with an appropriate solid or liquid carrier(s) or diluent(s). An appropriate adjuvant(s) (e.g. surfactants, adherents, dispersants, stabilizers) may be also admixed therein for improving the dispersibility and other properties of the composition.

Examples of the solid carriers of diluents are kaolin clay, attapulgite clay, bentonite, fuller's earth, pyrophyllite, talc, diatomaceous earth, calcite, corn stem powders, walnut-shell powders, fine powders or granules of urea, ammonium sulfate or synthetic hydrated silica, etc. Examples of the liquid carriers or diluents are aliphatic hydrocarbons (e.g. kerosene, lamp oil), aromatic hydrocarbons (e.g. benzene, toluene, xylene, methylnaphthalene), halogenated hydrocarbons (e.g. dichloroethane, trichloroethylene, carbon tetrachloride), alcohols (e.g. methanol, ethanol, isopropanol, ethylene glycol, cellosolve), ketones (e.g. acetone, methyl ethyl ketone, cyclohexanone, isophorone), ethers (e.g. diethyl ether, dioxane, tetrahydrofuran), esters (e.g. ethyl acetate), nitriles (e.g. acetonitrile, isobutylonitrile), acid amides (e.g. dimethylformamide, dimethylacetamide), dimethylsulfoxide, botanical oils (e.g. soybean oil, cotton-seed oil), etc.

Examples of the surfactants used for emulsification, dispersion or spreading may be any of ionic and non-ionic types. Examples of the ionic surfactants are alkylsulfates, alkylarylsulfonates, dialkylsulfosuccinates, phosphates of polyoxyethylene alkylaryl ether, condensates of naphthalenesulfonic acid and formalin, etc. Examples of the non-ionic surfactants are polyoxyethylene alkyl ethers, polyoxyethylene polyoxypropylene blocked copolymers, sorbitan fatty acid esters, polyoxyethylene sorbitan fatty acid esters, etc. Examples of the adherents and dispersants may include ligninsulfonates, alginates, polyvinyl alcohol, gum arabic, mollasses, casein, gelatin, CMC (carboxymethyl cellulose), pine seed oil, agar, etc. As the stabilizers, there may be used alkyl phosphates (e.g. isopropyl acid phosphate, tricresyl phosphate), botanical oils, epoxidized oils, various surfactants, antioxidizing agents (e.g. 2,6-di-t-butyl-p-cresol, mixture of 2-t-butyl-4-methoxyphenol and 3-t-butyl-4-methoxyphenol), aliphatic acid salts (e.g. sodium oleate, calcium stearate), aliphatic acid esters (e.g. methyl oleate, methyl stearate), etc.

The benzoylureas (I) of the invention formulated into an appropriate composition may be applied as such or in a form of dilution with water by a suitable method such as spraying, fumigating or smoking, or in combination with animal bait.

In addition, the composition may contain other insecticides, acaricides, nematocides, fungicides, herbicides, plant growth regulators, fertilizers, soil improvers, etc.

The dosage of the benzoylurea (I) as the active ingredient in an insecticidal agent is generally from 5 to 500 grams per 10 ares. When the composition is applied as an emulsifiable concentrate or a wettable powder, the concentration of the active ingredient may be normally from 10 to 1000 ppm. In case of such formulation as dusts, granules, oils, aerosoles, etc., the composition may be applied as such without diluting with water.

Some practical embodiments of the composition for the control of insects according to the invention are illustratively shown in the following Formulation Examples wherein % and part(s) are by weight.

FORMULATION EXAMPLE 1

Compound No. 3 (0.2 part), cyclohexanone (2 parts) and lamp oil (97.8 parts) are mixed well to make an oil preparation.

FORMULATION EXAMPLE 2

Anyone of Compound Nos. 1 to 12 (10 parts), polyoxyethylene styrylphenyl ether (14 parts), calcium dodecylbenzenesulfonate (6 parts), xylene (35 parts) and dimethylformamide (35 parts) are mixed well to make an emulsifiable concentrate preparation.

FORMULATION EXAMPLE 3

Compound No. 1 (20 parts), fenitrothion (O,O-dimethyl-O-(3-methyl-4-nitrophenyl)phosphorothioate) (10 parts), calcium ligninsulfonate (3 parts), sodium laurylsulfate (2 parts) and synthetic hydrated silica (65 parts) are mixed well in a pulverizer to make a wettable powder preparation.

FORMULATION EXAMPLE 4

Compound No. 2 (1 part), carbaryl (1-naphthyl N-methylcarbamate) (2 parts), kaolin clay (87 parts) and talc (10 parts) are mixed well in a pulverizer to give a dust preparation.

FORMULATION EXAMPLE 5

Compound No. 4 (5 parts), synthetic hydrated silica (1 part), calcium ligninsulfonate (2 parts), bentonite (30 parts) and kaolin clay (62 parts) are mixed well in a pulverizer. To the resultant mixture, water is added, and the resulting mixture is kneaded well and granulated by the aid of a granulator, followed by drying to give a granule preparation.

The following Test Examples show some typical test data indicating the excellent insecticidal activity of the benzoylureas (I). The compounds used for comparison are as follows:

| Compound No. | Chemical structure | Remarks |
| --- | --- | --- |
| A | 2,6-difluorophenyl-C(O)-NH-C(O)-NH-(4-chlorophenyl) | Diflubenzuron |
| B | $CH_3S(CH_3)C=N-O-C(O)-NHCH_3$ | Methomyl |
| C | 2,6-difluorophenyl-C(O)-NH-C(O)-NH-(4-(2,4-dichlorophenoxy)phenyl) | Compound disclosed in EP-57888A |

TEST EXAMPLE 1

An emulsifiable concentrate preparation formulated as in Formulation Example 2 was diluted with water to make a dilution containing the test compound in a concentration of 3.5 ppm. The dilution (100 ml) was charged in a plastic cup of 180 ml volume, and twenty last instar larvae of common mosquito (*Culex pipiens pallens*) were released therein. Feeding was continued up to emergence, and the rate of emergence was observed (two replications).

The results are shown in Table 3.

TABLE 3

| Compound No. | Rate of emergence (%) |
|---|---|
| 1 | 0 |
| 2 | 0 |
| 3 | 0 |
| 4 | 0 |
| 5 | 0 |
| 6 | 0 |
| 7 | 0 |
| 8 | 0 |
| 9 | 0 |
| 10 | 0 |
| 11 | 0 |
| 12 | 0 |
| Untreated | 87.5 |

TEST EXAMPLE 2

An emulsifiable concentrate preparation formulated as in Formulation Example 2 was diluted with water to make a designed dilution of the test compound. An artificial diet (13 g) for tobacco cutworm (*Spodoptera litura*) was impregnated with said dilution (2 ml) and placed into a polyethylene-made cup of 11 cm in diameter. Fourth larvae (10 insects) of tobacco cutworm were released therein. Six days thereafter, observation was made to determine the number of death, and the LC$_{50}$ value (i.e. lethal concentration to 50% death) was calculated therefrom (two replications). The results are shown in Table 4.

TABLE 4

| Compound No. | LC$_{50}$ (ppm) |
|---|---|
| 1 | 0.5 |
| 2 | 2.5 |
| 3 | 2.3 |
| 4 | 1.5 |
| 6 | 2.7 |
| 9 | 0.64 |
| 10 | 1.2 |
| 11 | 1.6 |
| A | 4.4 |
| B | 8.0 |
| C | 6.5 |

TEST EXAMPLE 3

An emulsifiable concentrate preparation formulated as in Formulation Example 2 was diluted with water to make a designed dilution of the test compound. Five grams of artificial diet placed into a polyethylene-made cup of 5.5 cm in diameter was impregnated with said dilution (1 ml). Ten-day old larvae (10 insects) of rice stem borer (*Chilo suppressalis*) were released therein. Eight days thereafter, observation was made to determine the number of death, and the LC$_{50}$ value was calculated therefrom (two replications). The results are shown in Table 5.

TABLE 5

| Compound No. | LC$_{50}$ (ppm) |
|---|---|
| 2 | 12 |
| 4 | 10 |
| 8 | 15 |

TEST EXAMPLE 4

Powdered animal feed (2 g) was thoroughly mixed with bran (14 g). An emulsifiable concentrate preparation formulated as in Formulation Example 2 was diluted with water to make a 10,000 fold dilution (corresponding to 10 ppm; 28 ml) and added to the above mixture. The resultant mixture was stirred well to make an artificial culture for housefly. Fifty nits of housefly (*Musca domestica*) were cultivated therein until their pupation. The obtained pupae were placed into a plastic cup, and the rate of emergence was observed. The results are shown in Table 6.

TABLE 6

| Compound No. | Rate of emergence (%) |
|---|---|
| 1 | 2 |
| 2 | 0 |
| 3 | 0 |
| 6 | 0 |
| Untreated | 92 |

What is claimed is:

1. A benzoylurea compound of the formula:

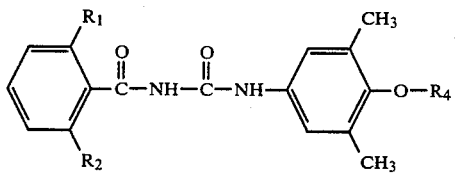

wherein R$_1$ is a hydrogen atom or a fluorine atom, R$_2$ is a fluorine atom or a chlorine atom, and R$_4$ is a 3,5-difluorophenyl group or a pentafluorophenyl group.

2. The compound according to claim 1, which is representable by the formula:

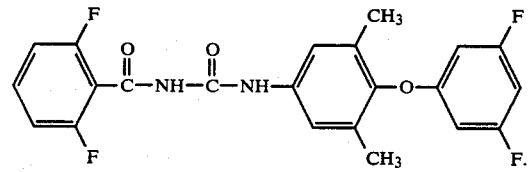

3. The compound according to claim 1, which is representable by the formula:

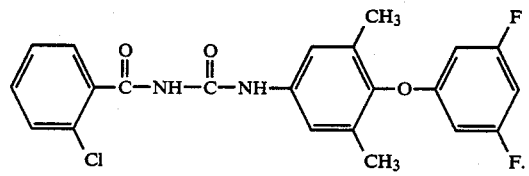

4. The compound according to claim 1, which is representable by the formula:

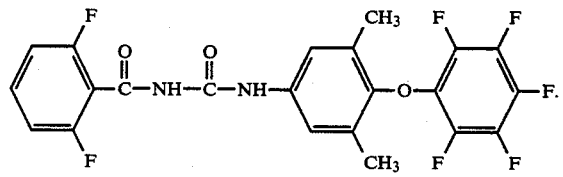

5. The compound according to claim 1, which is representable by the formula:

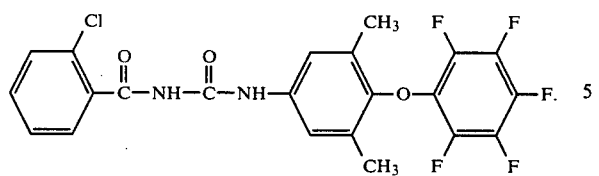

6. The compound according to claim 1, which is representable by the formula:

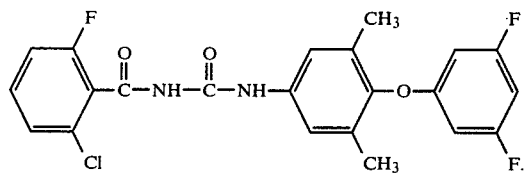

7. An insecticidal composition which comprises an insecticidally effective amount of the compound according to claim 1 and an inert carrier or diluent.

8. The composition according to claim 7, wherein the benzoylurea compound is representable by the formula:

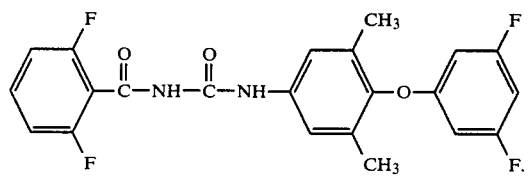

9. The composition according to claim 7, wherein the benzoylurea compound is representable by the formula:

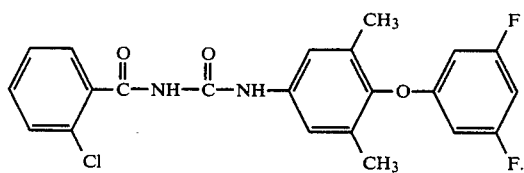

10. The composition according to claim 7, wherein the benzoylurea compound is representable by the formula:

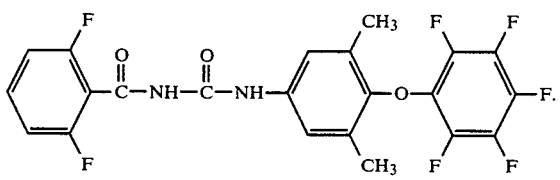

11. The composition according to claim 7, wherein the benzoylurea compound is representable by the formula:

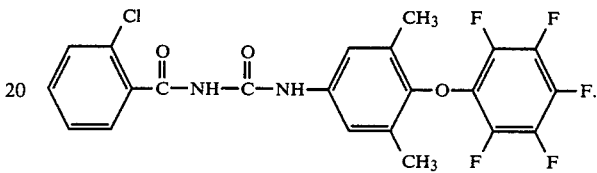

12. The composition according to claim 7, wherein the benzoylurea compound is representable by the formula:

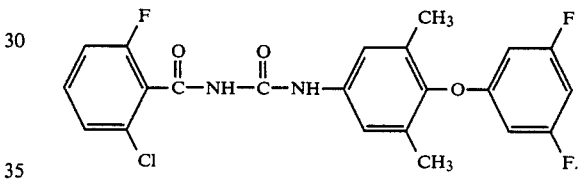

13. The composition according to claim 7, which is in the form of an emulsifiable concentrate, wettable powder, dust, granule, oil, aerozoles, fumigants or bait.

14. The composition according to claim 7, wherein the content of the benzoylurea is from 0.01 to 95% by weight.

15. The composition according to claim 13, wherein the composition is an emulsifiable concentrate or a wettable powder and the concentration of the benzoylurea ingredient in the emulsifiable concentrate or wettable powder is from 10 to 1000 ppm.

* * * * *